(12) United States Patent
Shaver et al.

(10) Patent No.: US 9,382,186 B1
(45) Date of Patent: *Jul. 5, 2016

(54) PROCESS FOR PRODUCING ACETIC ACID

(71) Applicant: Celanese International Corporation, Irving, TX (US)

(72) Inventors: Ronald D. Shaver, Houston, TX (US); Yaw-Hwa Liu, Missouri City, TX (US); Mark O. Scates, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/873,808

(22) Filed: Oct. 2, 2015

Related U.S. Application Data

(63) Continuation-in-part of application No. 14/788,928, filed on Jul. 1, 2015.

(51) Int. Cl.
*C07C 51/44* (2006.01)
*C07C 51/09* (2006.01)

(52) U.S. Cl.
CPC .............. *C07C 51/44* (2013.01); *C07C 51/09* (2013.01)

(58) Field of Classification Search
CPC ............................. C07C 51/44; C07C 51/09
USPC ....................................................... 562/608
See application file for complete search history.

(56) References Cited

U.S. PATENT DOCUMENTS

| | | | |
|---|---|---|---|
| 3,791,935 A | 2/1974 | Eubanks et al. |
| 4,008,131 A | 2/1977 | Price |
| 5,416,237 A | 5/1995 | Aubigne et al. |
| 5,880,311 A | 3/1999 | Uemura et al. |
| 6,225,498 B1 | 5/2001 | Blay et al. |
| 6,552,221 B1 | 4/2003 | Hallinan et al. |
| 6,657,078 B2 | 12/2003 | Scates et al. |
| 7,005,541 B2 | 2/2006 | Cheung et al. |
| 7,820,855 B2 | 10/2010 | Patt |
| 7,884,241 B2 | 2/2011 | Miura et al. |
| 8,940,932 B2 | 1/2015 | Shimizu |
| 8,957,248 B2 | 2/2015 | Miura et al. |
| 9,006,483 B2 | 4/2015 | Shimizu et al. |
| 9,073,843 B2 | 7/2015 | Shimizu et al. |

(Continued)

FOREIGN PATENT DOCUMENTS

| | | |
|---|---|---|
| JP | 4489487 B2 | 6/2010 |
| WO | 2014/115826 A1 | 7/2014 |

OTHER PUBLICATIONS

Zhu, Y. et al. (Apr. 2009). "Techno-economic Analysis for the Thermochemical Conversion of Lignocellulosic Biomass to Ethanol via Acetic Acid Synthesis," prepared for U.S. Department of Energy, PNNL-18483, Pacific Northwest National Laboratory, Richland, WA, 79 pages.

(Continued)

*Primary Examiner* — Jafar Parsa
*Assistant Examiner* — Amy C Bonaparte
(74) *Attorney, Agent, or Firm* — Kilpatrick Townsend & Stockton LLP

(57) ABSTRACT

A process for producing acetic acid is disclosed in which the water concentration is controlled in the side stream between two columns. Controlling the water concentration by the liquid light phase recycle controls the hydrogen iodide concentration in the side stream to be less than or equal to 50 wppm.

21 Claims, 1 Drawing Sheet

(56) References Cited

U.S. PATENT DOCUMENTS

| | | |
|---|---|---|
| 9,115,071 B2 | 8/2015 | Shimizu et al. |
| 2013/0264186 A1 | 10/2013 | Shimizu et al. |
| 2013/0281735 A1 | 10/2013 | Shimizu et al. |

OTHER PUBLICATIONS

Non-Final Office Action mailed on Sep. 11, 2015 for U.S. Appl. No. 14/788,928, 25 pages.

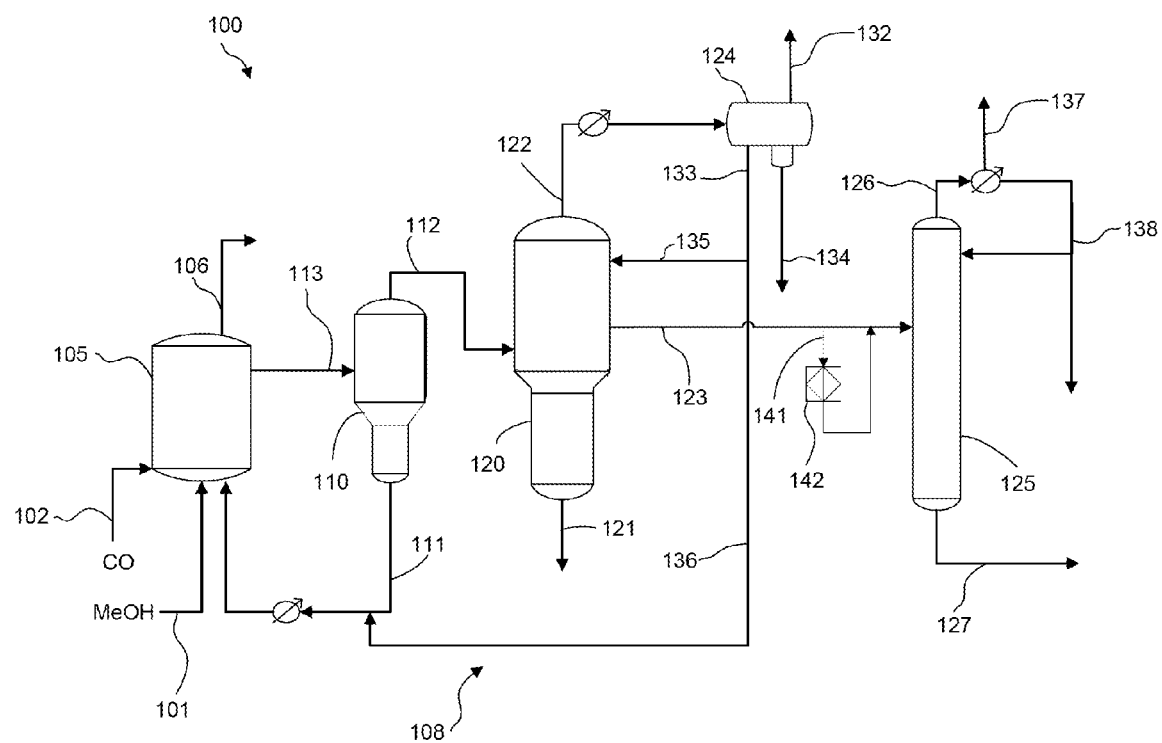

PROCESS FOR PRODUCING ACETIC ACID

CROSS-REFERENCES TO RELATED APPLICATIONS

This patent application is a continuation-in-part and claims priority from U.S. patent application Ser. No. 14/788,928, entitled "Process For Producing Acetic Acid," filed Jul. 1, 2015, the disclosure of which is incorporated herein by reference in its entirety.

FIELD OF THE INVENTION

This invention relates to processes for producing acetic acid and, in particular, to improved processes for controlling the water concentration and the hydrogen iodide concentration fed to the drying column.

BACKGROUND OF THE INVENTION

Among currently employed processes for synthesizing acetic acid, one of the most useful commercially is the catalyzed carbonylation of methanol with carbon monoxide as taught in U.S. Pat. No. 3,769,329, which is incorporated herein by reference in its entirety. The carbonylation catalyst contains a metal catalyst, such as rhodium, which is either dissolved or otherwise dispersed in a liquid reaction medium or supported on an inert solid, along with a halogen-containing catalyst promoter as exemplified by methyl iodide. The reaction is conducted by continuously bubbling carbon monoxide gas through a liquid reaction medium in which the catalyst is dissolved.

Methanol and carbon monoxide are fed to a reactor as feedstocks. A portion of the reaction medium is continuously withdrawn and provided to a flash vessel where the product is flashed and sent as a vapor to a purification train. The purification train includes a light ends column which removes "light" or low boiling components as an overhead and provides a side stream for further purification. The purification train may further include columns to dehydrate the side stream or for removing "heavy" or high boiling components, such as propionic acid, from the side stream. It is desirable in a carbonylation process for making acetic acid to minimize the number of distillation operations to minimize energy usage in the process.

U.S. Pat. No. 5,416,237 discloses a process for the production of acetic acid by carbonylation of methanol in the presence of a rhodium catalyst, methyl iodide, and an iodide salt stabilizer. The improvement according to the '237 patent resides in maintaining a finite concentration of water up to about 10 wt. % and a methyl acetate concentration of at least 2 wt. % in the liquid reaction composition and recovering the acetic acid product by passing the liquid reaction composition through a flash zone to produce a vapor fraction which is passed to a single distillation column from which the acetic acid product is removed. The drawback of eliminating distillation stages is that the level of purity of the product suffers. In particular, the distillation columns tend to remove high boiling iodides as well as aldehyde contamination products. Both of these impurities impact the commercial desirability of the final product.

U.S. Pat. No. 9,006,483 discloses a production process of acetic acid that seeks to inhibit concentration of hydrogen iodide and improves a liquid-liquid separation of an overhead from a distillation column. Acetic acid is produced by distilling a mixture containing hydrogen iodide, water, acetic acid and methyl acetate in a first distillation column to form an overhead and a side cut stream or bottom stream containing acetic acid, cooling and condensing the overhead in a condenser to form separated upper and lower phases in a decanter. According to this process, a zone having a high water concentration is formed in the distillation column above the feed position of the mixture by feeding a mixture having a water concentration of not less than an effective amount to not more than 5% by weight (e.g., 0.5 to 4.5% by weight) and a methyl acetate concentration of 0.5 to 9% by weight (e.g., 0.5 to 8% by weight) as the mixture to the distillation column and distilling the mixture. In the zone having a high water concentration, hydrogen iodide is allowed to react with methyl acetate to produce methyl iodide and acetic acid.

U.S. Pat. No. 7,884,241 discloses a mixture containing hydrogen iodide and water and having a water content of not more than 5% by weight (particularly not more than 3% by weight) in a distillation system that is distilled to prevent condensation of hydrogen iodide in the distillation system. The mixture may comprise hydrogen iodide, water, methanol, methyl iodide, acetic acid, and methyl acetate. Even when the mixture contains hydrogen iodide at a concentration of 1 to 3000 ppm on the basis of weight, an acetic acid product having a concentration of hydrogen iodide of not more than 50 ppm can be obtained by withdrawing a fraction containing hydrogen iodide from the top of the column and withdrawing acetic acid as a side-cut stream or a stream from the bottom of the column. Such a process (distillation process) effectively inhibits condensation of hydrogen iodide in the distillation system and corrosion in the distillation system. To keep water concentrations low, this process requires a large reflux of 2.35, which is energy intensive.

U.S. Pat. No. 6,657,078 discloses a low energy process for producing acetic acid by the carbonylation of methanol. The process involves a rhodium-catalyzed system operated at less than about 14 wt. % water utilizing up to 2 distillation columns.

U.S. Pat. No. 4,008,131 discloses a method for removal of excess water which tends to build up in recycle streams and reduces the rate of pure acid production during operation of a distillation system for purification of crude acetic acid containing water and methyl iodide. The crude acid is introduced into the upper half of a distillation zone. The methyl iodide, a major proportion of water and an equivalent amount of acid are removed overhead from the zone. A minor proportion of the water containing a small amount of acetic acid is removed as a liquid sidedraw at a point near the top of the distillation zone. A product acid stream essentially dry and substantially free of methyl iodide is removed from the bottom of the distillation zone. The overhead stream can be stored, disposed of or preferably recycled to the acid-producing step. The liquid water sidedraw may either be discarded or subjected to rectification for recovery of acid values.

U.S. Pat. No. 3,791,935 discloses a process by introducing a monocarboxylic acid stream containing water and the halogen contaminant into the upper half of a distillation column, removing an overhead fraction consisting primarily of the water and alkyl halide charged to said column, removing a stream from the middle portion of said column containing a major proportion of hydrogen halide present in said column, and removing a product acid stream from at or near the bottom of said column, the product acid stream being essentially dry and substantially free of the halogen contaminants charged to said column. The method is particularly applicable to the removal of water and iodine-containing compounds from acetic and propionic acids. In the examples, the bottoms product that contains acetic acid is reported to contain from 83 to 132 wppm water and 0.083 wppm to 0.3 wppm hydrogen iodide.

In view of the foregoing, the need exists for an improved acetic acid production process to control recovery of acetic acid.

SUMMARY OF THE INVENTION

In one embodiment the present invention relates to a process for producing acetic acid comprising separating a reaction medium formed in a reactor in a flash vessel to form a liquid recycle and a vapor product stream, distilling the vapor product stream in a first column to obtain a side stream and a low boiling overhead vapor stream comprising water in an amount of greater than or equal to 5 wt. %, condensing the low boiling overhead vapor stream and biphasically separating the condensed stream to form a heavy liquid phase and a light liquid phase, maintaining a water concentration in the side stream from 1 to 3 wt. %, e.g., preferably from 1.1 to 2.5 wt. %, and a hydrogen iodide concentration in the side stream in an amount of less than or equal to 50 wppm, e.g., preferably from 0.1 to 50 wppm, by controlling a recycle rate of the light liquid phase to the reactor, and distilling the side stream in a second column to obtain a purified acetic acid product. The side stream may further comprise one or more $C_1$-$C_{14}$ alkyl iodides in an concentration from 0.1 to 6 wt. %, and the side stream further comprises methyl acetate in an concentration from 0.1 to 6 wt. %. In one embodiment, the side stream comprises each of the one or more $C_1$-$C_{14}$ alkyl iodides and the methyl acetate in an amount ±0.9 wt. % of the water concentration in the side stream. The reaction medium may further comprise methyl acetate, a metal catalyst, an iodide salt and methyl iodide. In one embodiment, the reaction medium comprises methyl acetate in an amount from 0.5 to 30 wt. %, a metal catalyst in an amount from 200 to 3000 wppm, iodide salt in an amount from 1 to 25 wt. %, and methyl iodide in an amount from 1 to 25 wt. %. In a further embodiment, a portion of the heavy liquid phase is treated to remove at least one permanganate reducing compound selected from the group consisting of acetaldehyde, acetone, methyl ethyl ketone, butylaldehyde, crotonaldehyde, 2-ethyl crotonaldehyde, 2-ethyl butyraldehyde, and the aldol condensation products thereof. The process may involve refluxing the heavy liquid phase, the light liquid phase, or a mixture thereof to the first column. In one embodiment, the first column is operated with a reflux ratio from 0.05 to 0.4. Water from condensing the low boiling overhead vapor stream is primarily collected in the light liquid phase, and in one embodiment, the light liquid phase comprises water in an amount from 40 to 80 wt. %, and the heavy liquid phase comprises water in an amount of less than or equal to 1 wt. %. The purified acetic acid product may be withdrawn from the bottoms or near the bottoms of the second column, and an aqueous overhead is withdrawn from the second column. In one embodiment, the aqueous overhead comprises greater than or equal to 90% of the water in the side stream fed to the second column. The process may further comprise recycling the aqueous overhead, or a condensed portion thereof, to the reactor, wherein the recycle ratio of the mass flow of the light liquid phase recycled to the reactor to the mass flow of the aqueous overhead to the reactor is less than or equal to 2. In some embodiment, water, methyl acetate, or a combination thereof is not introduced to the vapor stream or to the first column. The process may further comprise contacting the purified acetic acid product with a guard bed when total iodide concentration of the purified acetic acid product is less than or equal to 5 wppm. In one embodiment, the recycle of light liquid phase is from 0 to 20%, of the total light phase condensed from the low boiling overhead vapor stream.

In another embodiment the present invention relates to a process for producing acetic acid comprising separating a reaction medium formed in a reactor in a flash vessel to form a liquid recycle and a vapor product stream, wherein the reaction medium comprises water in an amount from 0.1 to 4.1 wt. %, distilling a portion of the vapor product stream in a first column to obtain a side stream, a low boiling overhead vapor stream comprising water in an amount of greater than or equal to 5 wt. %, and a residuum stream comprising acetic acid in an amount greater than or equal to 95 wt. % and water in an amount less than or equal to 5 wt. %, condensing the low boiling overhead vapor stream and biphasically separating the condensed stream to form a heavy liquid phase and a light liquid phase, maintaining a water concentration in the side stream from 1 to 3 wt. % and a hydrogen iodide concentration in the side stream of less than or equal to 50 wppm, e.g., preferably from 0.1 to 50 wppm, based on the total weight of the side stream by controlling a recycle rate of a portion of the light liquid phase to the reactor, and distilling the side stream in a second column to obtain a purified acetic acid product. The side stream may further comprise one or more $C_1$-$C_{14}$ alkyl iodides in an concentration from 0.1 to 6 wt. %, and the side stream further comprises methyl acetate in an concentration from 0.1 to 6 wt. %. In one embodiment, the side stream comprises each of the one or more $C_1$-$C_{14}$ alkyl iodides and the methyl acetate in an amount ±0.9 wt. % of the water concentration in the side stream. The reaction medium may further comprise methyl acetate, a metal catalyst, an iodide salt and methyl iodide. In one embodiment, the reaction medium comprises methyl acetate in an amount from 0.5 to 30 wt. %, a metal catalyst in an amount from 200 to 3000 wppm, iodide salt in an amount from 1 to 25 wt. %, and methyl iodide in an amount from 1 to 25 wt. %. In a further embodiment, a portion of the heavy liquid phase is treated to remove at least one permanganate reducing compound selected from the group consisting of acetaldehyde, acetone, methyl ethyl ketone, butylaldehyde, crotonaldehyde, 2-ethyl crotonaldehyde, 2-ethyl butyraldehyde, and the aldol condensation products thereof. The process may involve refluxing the heavy liquid phase, the light liquid phase, or a mixture thereof to the first column. In one embodiment, the first column is operated with a reflux ratio from 0.05 to 0.4. Water from condensing the low boiling overhead vapor stream is primarily collected in the light liquid phase, and in one embodiment, the light liquid phase comprises water in an amount from 40 to 80 wt. %, and the heavy liquid phase comprises water in an amount of less than or equal to 1 wt. %. The purified acetic acid product may be withdrawn from the bottoms or near the bottoms of the second column, and an aqueous overhead is withdrawn from the second column. In one embodiment, the aqueous overhead comprises greater than or equal to 90% of the water in the side stream fed to the second column. The process may further comprise recycling the aqueous overhead, or a condensed portion thereof, to the reactor, wherein the recycle ratio of the mass flow of the light liquid phase recycled to the reactor to the mass flow of the aqueous overhead to the reactor is less than or equal to 2. In some embodiment, water, methyl acetate, or a combination thereof is not introduced to the vapor stream or to the first column. The process may further comprise contacting the purified acetic acid product with a guard bed when total iodide concentration of the purified acetic acid product is less than or equal to 5 wppm. In one embodiment, the recycle rate of light liquid phase is from 0 to 20%, of the total light phase condensed from the low boiling overhead vapor stream.

In yet another embodiment, the present invention relates to a process for producing acetic acid comprising separating a reaction medium formed in a reactor in a flash vessel to form a liquid recycle and a vapor product stream, distilling the vapor product stream in a first column to obtain a side stream and a low boiling overhead vapor stream, condensing the low boiling overhead vapor stream and biphasically separating the condensed stream to form a heavy liquid phase and a light liquid phase, measuring hydrogen iodide concentration in the side stream, controlling recycle rate of the light liquid phase to the reactor in response to the measured hydrogen iodide to maintain hydrogen iodide concentration in the side stream of less than or equal to 50 wppm, and distilling the side stream in a second column to obtain a purified acetic acid product.

In a further embodiment, the present invention relates to a process for producing acetic acid comprising separating a reaction medium formed in a reactor in a flash vessel to form a liquid recycle and a vapor product stream, distilling the vapor product stream in a first column to obtain a low boiling overhead vapor stream and a side stream comprising water in an amount from 1 to 3 wt. %, one or more $C_1$-$C_{14}$ alkyl iodides in an amount from 0.1 to 6 wt. %, and hydrogen iodide in an amount of less than or equal to 50 wppm, distilling the side stream in a second column to obtain a purified acetic acid product, and contacting the purified acetic acid product with a guard bed when total iodide concentration of the purified acetic acid product is less than or equal to 5 wppm, e.g., less than or equal to 1 wppm.

BRIEF DESCRIPTION OF THE DRAWING

The present invention will be better understood in view of the appended non-limiting figure, wherein:

FIG. 1 is a schematic drawing for producing acetic acid in accordance with the present invention.

DETAILED DESCRIPTION OF THE INVENTION

At the outset, it should be noted that in the development of any such actual embodiment, numerous implementation-specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, a range "from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise specified.

As used in the specification and claims, "near" is inclusive of "at." The term "and/or" refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

All percentages are expressed as weight percent (wt. %), based on the total weight of the particular stream or composition present, unless otherwise noted. Room temperature is 25° C. and atmospheric pressure is 101.325 kPa unless otherwise noted.

For purposes herein:
acetic acid may be abbreviated as "AcOH";
acetaldehyde may be abbreviated as "AcH";
methyl acetate may be abbreviated "MeAc";
methanol may be abbreviated "MeOH";
methyl iodide may be abbreviated as "MeI";
hydrogen iodide may be abbreviated as "HI";
carbon monoxide may be abbreviated "CO"; and
dimethyl ether may be abbreviated "DME".

HI refers to either molecular hydrogen iodide or dissociated hydriodic acid when at least partially ionized in a polar medium, typically a medium comprising at least some water. Unless otherwise specified, the two are referred to interchangeably. Unless otherwise specified, HI concentration is determined via acid-base titration using a potentiometric end point. In particular, HI concentration is determined via titration with a standard lithium acetate solution to a potentiometric end point. It is to be understood that for purposes herein, the concentration of HI is not determined by subtracting a concentration of iodide assumed to be associated with a measurement of corrosion metals or other non H+ cations from the total ionic iodide present in a sample.

It is to be understood that HI concentration does not refer to iodide ion concentration. HI concentration specifically refers to HI concentration as determined via potentiometric titration.

This subtraction method is an unreliable and imprecise method to determine relatively lower HI concentrations (i.e., less than or equal to 5 weight percent) due to the fact that it assumes all non-H+ cations (such as cations of Fe, Ni, Cr, Mo) are associated with iodide anion exclusively. In reality, a significant portion of the metal cations in this process can be associated with acetate anion. Additionally, many of these metal cations have multiple valence states, which adds even more unreliability to the assumption on the amount of iodide anion which could be associated with these metals. Ultimately, this method gives rise to an unreliable determination of the actual HI concentration, especially in view of the ability to perform a simple titration directly representative of the HI concentration.

For purposes herein, an "overhead" or "distillate" of a distillation column refers to at least one of the lower boiling condensable fractions which exits at or near the top, (e.g., proximate to the top), of the distillation column, and/or the condensed form of that stream or composition. Obviously, all fractions are ultimately condensable, yet for purposes herein, a condensable fraction is condensable under the conditions present in the process as readily understood by one of skill in the art. Examples of noncondensable fractions may include nitrogen, hydrogen, and the like. Likewise, an overhead stream may be taken just below the upper most exit of a distillation column, for example, wherein the lowest boiling fraction is a non-condensable stream or represents a de-minimis stream, as would be readily understood by one of reasonable skill in the art.

The "bottoms" or "residuum" of a distillation column refers to one or more of the highest boiling fractions which exit at or near the bottom of the distillation column, also referred to herein as flowing from the bottom sump of the column. It is to be understood that a residuum may be taken from just above the very bottom exit of a distillation column, for example, wherein the very bottom fraction produced by the column is a salt, an unusable tar, a solid waste product, or a de-minimis stream as would be readily understood by one of reasonable skill in the art.

For purposes herein, distillation columns comprise a distillation zone and a bottom sump zone. The distillation zone includes everything above the bottom sump zone, i.e., between the bottom sump zone and the top of the column. For purposes herein, the bottom sump zone refers to the lower portion of the distillation column in which a liquid reservoir of the higher boiling components is present (e.g., the bottom of a distillation column) from which the bottom or residuum stream flows upon exiting the column. The bottom sump zone may include reboilers, control equipment, and the like.

It is to be understood that the term "passages", "flow paths", "flow conduits", and the like in relation to internal components of a distillation column are used interchangeably to refer to holes, tubes, channels, slits, drains, and the like, which are disposed through and/or which provide a path for liquid and/or vapor to move from one side of the internal component to the other side of the internal component. Examples of passages disposed through a structure such as a liquid distributor of a distillation column include drain holes, drain tubes, drain slits, and the like, which allow a liquid to flow through the structure from one side to another.

Average residence time is defined as the sum total of all liquid volume hold-up for a given phase within a distillation zone divided by the average flow rate of that phase through the distillation zone. The hold-up volume for a given phase can include liquid volume contained in the various internal components of the column including collectors, distributors and the like, as well as liquid contained on trays, within downcomers, and/or within structured or random packed bed sections.

Controlling Recycle Rate

The present invention provides methods for controlling the water concentration in the side stream between two columns in acetic acid recovery process. The side stream primarily comprises acetic acid produced by carbonylation. In controlling the water concentration, the hydrogen iodide concentration may also be regulated to reduce the amount of hydrogen iodide that is forwarded from a light ends column or first column to a drying column or second column for subsequent acetic acid recovery. Advantageously, the water concentration may be controlled by the recycle rate of the light liquid phase recovered from the first column to the reactor. In one embodiment, 0 to 20% of the total light liquid phase condensed from the low boiling overhead vapor stream is recycled and the remainder may be used as a reflux on the light ends column or fed to an acetaldehyde reduction system. Because the light liquid phase is also refluxed to the first column, a change in the reflux ratio may also affect the recycle rate. Reducing the hydrogen iodide fed to the second column helps to reduce the total iodide concentration in the second column and ultimately the purified acetic acid product. A low total iodide concentration, e.g., less than or equal to 5 wppm, or less than or equal to 1 wppm, in the purified acetic acid product allows for removal of iodide by using a guard bed. This greatly improves the quality of the purified acetic acid product.

In one embodiment, there is provided a process for producing acetic acid comprising separating a reaction medium formed in a reactor in a flash vessel to form a liquid recycle and a vapor product stream, distilling the vapor product stream in a first column to obtain a side stream and a low boiling overhead vapor stream comprising water in an amount of greater than or equal to 5 wt. %, condensing the low boiling overhead vapor stream and biphasically separating the condensed stream to form a heavy liquid phase and a light liquid phase, maintaining a water concentration in the side stream from 1 to 3 wt. %, e.g., preferably from 1.1 to 2.5 wt. %, and a hydrogen iodide concentration in the side stream in an amount of less than or equal to 50 wppm, e.g., preferably from 0.1 to 50 wppm, by controlling a recycle rate of the light liquid phase to the reactor, and distilling the side stream in a second column to obtain a purified acetic acid product.

Under low water conditions in the reactor, e.g., when the water concentration is from 0.1 to 4.1 wt. %, operating the distillation column in a stable manner may be difficult while maintaining low levels of water in the reactor. As water concentration decreases maintaining stable operating of the distillation columns may be disrupted when there is not sufficient water in the columns. Although adding water to the columns may overcome this problem, it is not desirable because 1) this requires either a larger purge of water and more energy in separation, and/or 2) may result in increasing the water recycled to the reactor that disrupts the reactor conditions. Thus, in one embodiment, there is provided a process for producing acetic acid comprising separating a reaction medium formed in a reactor in a flash vessel to form a liquid recycle and a vapor product stream, wherein the reaction medium comprises water in an amount from 0.1 to 4.1 wt. %, distilling a portion of the vapor product stream in a first column to obtain a side stream, a low boiling overhead vapor stream comprising water in an amount of greater than or equal to 5 wt. %, and a residuum stream comprising acetic acid in an amount greater than or equal to 95 wt. % and water in an amount less than or equal to 5 wt. %, condensing the low boiling overhead vapor stream and biphasically separating the condensed stream to form a heavy liquid phase and a light liquid phase, maintaining a water concentration in the side stream from 1 to 3 wt. % and a hydrogen iodide concentration in the side stream of less than or equal to 50 wppm, e.g., preferably from 0.1 to 50 wppm, based on the total weight of the side stream by controlling a recycle rate of a portion of the light liquid phase to the reactor, and distilling the side stream in a second column to obtain a purified acetic acid product.

As provided herein, the hydrogen iodide concentration in the side stream may be measured to control the recycle rate of the light liquid phase. In another embodiment, there is provided a process for producing acetic acid comprising separating a reaction medium formed in a reactor in a flash vessel to form a liquid recycle and a vapor product stream, distilling the vapor product stream in a first column to obtain a side stream and a low boiling overhead vapor stream, condensing the low boiling overhead vapor stream and biphasically separating the condensed stream to form a heavy liquid phase and a light liquid phase, measuring hydrogen iodide concentration in the side stream, controlling recycle rate of the light liquid phase to the reactor in response to the measured hydrogen iodide to maintain hydrogen iodide concentration in the side stream of less than or equal to 50 wppm, and distilling the side stream in a second column to obtain a purified acetic acid product.

In yet another embodiment, there is provided a process for producing acetic acid comprising separating a reaction medium formed in a reactor in a flash vessel to form a liquid recycle and a vapor product stream, distilling the vapor product stream in a first column to obtain a low boiling overhead vapor stream and a side stream comprising water in an amount from 1 to 3 wt. %, one or more $C_1$-$C_{14}$ alkyl iodides in an amount from 0.1 to 6 wt. %, and hydrogen iodide in an amount of less than or equal to 50 wppm, distilling the side stream in a second column to obtain a purified acetic acid product, and contacting the purified acetic acid product with a guard bed when total iodide concentration of the purified acetic acid product is less than or equal to 5 wppm, e.g., less than or equal to 1 wppm.

In addition to maintaining low levels of hydrogen iodide in the side stream it is also advantageous to feed the second column a stable amount of other reactor components and impurities, such as $C_1$-$C_{14}$ alkyl iodides, namely methyl iodide, and methyl acetate. Along with water, the $C_1$-$C_{14}$ alkyl iodides and methyl acetate may be removed and returned to the reactor. By controlling the water concentration in the side stream to be in amount from 1 to 3 wt. %, the present invention may also maintain stable amount of $C_1$-$C_{14}$ alkyl iodides and methyl acetate relative to the water concentration. By stable amount it is meant that the concentration of the one or more $C_1$-$C_{14}$ alkyl iodides and the concentration of methyl acetate is within the range of ±0.9% of the water concentration in the side stream, e.g., ±0.7%, ±0.6%, ±0.5%, ±0.4%, ±0.3%, ±0.2%, or ±0.1%. For example, when the water concentration is 2.5 wt. %, the concentration of $C_1$-$C_{14}$ alkyl iodides is from 1.6 to 3.4 wt. %, and the concentration of methyl acetate is from 1.6 to 3.4 wt. %. This may be achieved by controlling a recycle rate of a portion of the light liquid phase to the reactor. In some embodiments, controlling the recycle rate of a portion of the light liquid phase to the reactor may achieve a stable concentration of methyl iodide in the side stream within the range of ±0.6% of the water concentration in the side stream, e.g., ±0.5%, ±0.4%, ±0.3%, ±0.2%, or ±0.1%.

In one embodiment, there is provided a process for producing acetic acid comprising separating a reaction medium formed in a reactor in a flash vessel to form a liquid recycle and a vapor product stream, wherein the reaction medium comprises water in an amount from 0.1 to 4.1 wt. % and methyl acetate in an amount of less than or equal to 9 wt. %, distilling a portion of the vapor product stream in a first column to obtain a side stream comprising acetic acid, water, hydrogen iodide, one or more $C_1$-$C_{14}$ alkyl iodides, and methyl acetate, a low boiling overhead vapor stream comprising water in an amount of greater than or equal to 5 wt. %, and a residuum stream comprising acetic acid in an amount greater than or equal to 95 wt. % and water in an amount less than or equal to 5 wt. %, condensing the low boiling overhead vapor stream and biphasically separating the condensed stream to form a heavy liquid phase and a light liquid phase, maintaining a water concentration in the side stream from 1 to 3 wt. % and a hydrogen iodide concentration in the side stream of less than or equal to 50 wppm, based on the total weight of the side stream by controlling a recycle rate of a portion of the light liquid phase to the reactor, and wherein the side stream comprises each of the one or more $C_1$-$C_{14}$ alkyl iodides and the methyl acetate in an amount ±0.9 wt. % of the water concentration in the side stream and distilling the side stream in a second column to obtain a purified acetic acid product.

By controlling the recycle rate of the liquid light phase, the concentration of the components, in particular water and hydrogen iodide, in the side stream between two columns may be maintained within certain concentration limits. The recycle of the light liquid phase results in a side stream comprising water in an amount from 1 to 3 wt. %, e.g., from 1 to 2.5 wt. % and more preferably from 1.1 to 2.1 wt. %. In embodiments, the concentration of water in the side stream is maintained at greater than or equal to 1 wt. %, or greater than or equal to 1.1 wt. %, or greater than or equal to 1.3 wt. %, or greater than or equal to 1.5 wt. %, or greater than or equal to 2 wt. %, and/or in embodiments, the concentration of water in the side stream is maintained at less than or equal to 3 wt. %, or less than or equal to 2.8 wt. %, or less than or equal to 2.5 wt. %, or less than or equal to 2.1 wt. %. A water concentration within this range maintains a certain amount of hydrogen iodide of less than or equal to 50 wppm in the side stream, e.g., from 0.1 to 50 wppm hydrogen iodide, or from 5 to 30 wppm hydrogen iodide. In embodiments, the concentration of hydrogen iodide in the side stream is maintained at less than or equal to 50 wppm, or less than or equal to 45 wppm, or less than or equal to 40 wppm, or less than or equal to 35 wppm, or less than or equal to 30 wppm, and/or in embodiments, the concentration of hydrogen iodide in the side stream is maintained at greater than or equal to 0.1 wppm, or greater than or equal to 1 wppm, or greater than or equal to 5 wppm, or greater than or equal to 10 wppm.

Controlling the recycle rate of the liquid light phase to maintain the water concentration in the side stream as described above also maintains certain water concentrations in the overhead and bottoms in the first column. In embodiments, the concentration of water in the overhead is maintained at greater than or equal to 5 wt. %, or greater than or equal to 10 wt. %, or greater than or equal to 15 wt. %, or greater than or equal to 20 wt. %, or greater than or equal to 25 wt. %, and/or in embodiments, the concentration of water in the overhead is maintained at less than or equal to 80 wt. %, or less than or equal to 75 wt. %, or less than or equal to 70 wt. %, or less than or equal to 60 wt. %. Under low water conditions in the reaction medium, e.g., water in an amount from 0.1 to 4.1 wt. %, it is desirable to maintain low concentrations of water in the bottom of the first column. Having water in excess of 5 wt. % is not desirable to stably operate the purification system of the present invention. Thus, in embodiments, the concentration of water in the bottoms is maintained at less than or equal to 5 wt. %, or less than or equal to 4.5 wt. %, or less than or equal to 4 wt. %, or less than or equal to 3.5 wt. %, or greater than or equal to 3 wt. %, and/or in embodiments, the concentration of water in the bottoms is maintained at greater than or equal to 0 wt. %, or greater than or equal to 0.5 wt. %, or greater than or equal to 1 wt. %, or greater than or equal to 1.5 wt. %.

Hydrogen iodide is soluble in acetic acid-water mixtures containing water in an amount from 3 to 8 wt. % and the solubility of hydrogen iodide decreases as the water concentration decreases. This makes hydrogen iodide more volatile and thus, in some embodiments, hydrogen iodide may be collected in the overhead of the column. Although hydrogen iodide has been indicated by others to be corrosive, a certain amount of hydrogen iodide under some conditions may be beneficial to act as a catalyst, such as a catalyst for forming dimethyl ether as described in U.S. Pat. No. 7,223,883, the entire contents and disclosures of which are incorporated by reference.

The control of the recycle of the liquid light phase is an improvement over other processes that maintain concentrations of the vapor product feeding the first column, such as those described in U.S. Pat. No. 9,006,483. The present invention advantageously improves control for any type of feed without having to introduce additional components into the first column or maintain concentrations in a vapor product feed. Thus, in embodiments, the present invention does not feed water or methyl acetate into the first column or the feed source, i.e. vapor stream, into the first column. In addition, U.S. Pat. No. 9,006,483 fails to control the light liquid phase recycle to the reactor and thus cannot independently control the water and hydrogen iodide concentration in the side stream.

By controlling a recycle rate of a portion of the light liquid phase allows the present invention to concentrate the major component, acetic acid, in the side stream. Thus, the side stream comprises acetic acid in amount of greater than or equal to 90 wt. %, e.g., greater than or equal to 94 wt. % or greater than or equal to 96 wt. %. In terms of ranges, the acetic acid concentration may be in an amount from 90 to 99 wt. %, e.g., from 91 to 98 wt. %. This allows a majority of the acetic acid fed to the first column to be withdrawn in the side stream for further purification. Preferably, acetic acid is not recovered as a product in the overhead or bottoms of the first column.

In addition to acetic acid and water, the side stream may also comprise one or more $C_1$-$C_{14}$ alkyl iodides in an amount from 0.1 to 6 wt. %, e.g., from 0.5 to 5 wt. %, from 0.6 to 4 wt. %, from 0.7 to 3.7 wt. %, or from 0.8 to 3.6 wt. %. In one embodiment, the one or more $C_1$-$C_{14}$ alkyl iodides at least comprise methyl iodide. Other alkyl iodides such as hexyl iodide may also be formed from carbonyl impurities such as acetaldehyde. More preferably, the side stream comprises one or more $C_1$-$C_{14}$ alkyl iodides in an amount from 0.5 to 3 wt. %. Due to the presence of water, the side stream may also contain methyl acetate in an amount from 0.1 to 6 wt. %, e.g., from 0.5 to 5 wt. %, from 0.6 to 4 wt. %, from 0.7 to 3.7 wt. %, or from 0.8 to 3.6 wt. %. As indicated herein, in embodiments, there may be a stable amount of other reactor components and impurities, such as $C_1$-$C_{14}$ alkyl iodides, namely methyl iodide, and methyl acetate in the side stream based on the water concentration.

Others have determined hydrogen iodide content indirectly by calculation. US Pub. No. 2013/0310603, for example, indicates that iodide ion concentration may be calculated by subtracting the iodide ion concentration derived from the iodide salt form (including iodides derived from co-catalysts and metal iodide) from the total concentration of iodide ion ($I^-$). Such indirect calculation techniques are typically inaccurate, resulting in a poor indication of actual hydrogen iodide concentration owing largely to the inaccuracies of the underlying ion measurement methods. In addition, this indirect calculation technique fails to account for other iodide forms because metal cations are measured and incorrectly assumed to be completely associated only with iodide anions while, in fact, the metal cations may be associated with other anions, such as acetate and catalyst anions. In contrast, the direct measurement of hydrogen iodide concentration according to the present invention advantageously reflects the actual hydrogen iodide concentration in the system, and can result in accuracy as low as 0.01%. In one embodiment, the hydrogen iodide concentration in the side stream may be determined by potentiometric titration using lithium acetate as the titrant.

By detecting the hydrogen iodide concentration of the side stream, the recycle rate of the light liquid phase may be controlled. For example, when the hydrogen iodide concentration exceeds a determined threshold of 50 wppm, the recycle rate of the light liquid phase may be increased. Once the hydrogen iodide concentration is below the determined threshold of 50 wppm, the recycle rate of the light liquid phase may be maintained and/or decreased as desired to also maintain water concentrations in an amount from 1 to 3 wt. %. As described herein, the recycle rate of the light liquid phase is the amount being recycled as compared to the amount of light liquid phase being refluxed. The light liquid phase may be recycled directly to the carbonylation reactor or indirectly by first removing an impurity, such as a carbonyl compound, prior to recycling to the reactor.

Reaction Step

Exemplary reaction and acetic acid recovery system 100 is shown in FIG. 1. As shown, methanol-containing feed stream 101 and carbon monoxide-containing feed stream 102 are directed to liquid phase carbonylation reactor 105, in which the carbonylation reaction occurs to form acetic acid.

Methanol-containing feed stream 101 may comprise at least one member selected from the group consisting of methanol, dimethyl ether, and methyl acetate. Methanol-containing feed stream 101 may be derived in part from a fresh feed or may be recycled from the system. At least some of the methanol and/or reactive derivative thereof will be converted to, and hence present as, methyl acetate in the liquid medium by esterification with acetic acid.

Typical reaction temperatures for carbonylation will be from 150 to 250° C., with the temperature range of 180 to 225° C. being a preferred range. The carbon monoxide partial pressure in the reactor may vary widely but is typically from 2 to 30 atm, e.g., from 3 to 10 atm. The hydrogen partial pressure in the reactor is typically from 0.05 to 2 atm, e.g., from 0.25 to 1.9 atm. In some embodiments, the present invention may be operated with a hydrogen partial pressure from 0.3 to 2 atm, e.g., from 0.3 to 1.5 atm, or from 0.4 to 1.5 atm. Because of the partial pressure of by-products and the vapor pressure of the contained liquids, the total reactor pressure will range from 15 to 40 atm. The production rate of acetic acid may be from 5 to 50 mol/L·h, e.g., from 10 to 40 mol/L·h, and preferably 15 to 35 mol/L·h.

Carbonylation reactor 105 is preferably either a mechanically stirred vessel, a vessel with an educted or pump-around mixing, or bubble-column type vessel, with or without an agitator, within which the reacting liquid or slurry contents are maintained, preferably automatically, at a predetermined level, which preferably remains substantially constant during normal operation. Into carbonylation reactor 105, fresh methanol, carbon monoxide, and sufficient water are continuously introduced as needed to maintain suitable concentrations in the reaction medium.

The metal catalyst may comprise a Group VIII metal. Suitable Group VIII catalysts include rhodium and/or iridium catalysts. When a rhodium catalyst is used, the rhodium catalyst may be added in any suitable form such that rhodium is in the catalyst solution as an equilibrium mixture including [Rh(CO)$_2$I$_2$]-anion, as is well known in the art. Iodide salts optionally maintained in the reaction mixtures of the processes described herein may be in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The catalyst co-promoter may be added as a non-iodide salt that will generate an iodide salt. The catalyst co-promoter may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding catalyst co-promoter. For additional detail regarding rhodium catalysis and iodide salt generation, see U.S. Pat. Nos. 5,001,259; 5,026,908; 5,144,068 and 7,005,541, which are incorporated herein by reference in their entirety. The carbonylation of methanol utilizing iridium catalyst is well known and is generally described in U.S. Pat. Nos. 5,942,460, 5,932,764, 5,883,295, 5,877,348, 5,877,347 and 5,696,284, which are incorporated herein by reference in their entirety.

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide.

The components of the reaction medium are maintained within defined limits to ensure sufficient production of acetic acid. The reaction medium contains a concentration of the metal catalyst, e.g., rhodium catalyst, in an amount from 200 to 3000 wppm, e.g., from 800 to 3000 wppm, or from 900 to 1500 wppm. The concentration of water in the reaction medium is maintained to be less than or equal to 14 wt. %, e.g., from 0.1 wt. % to 14 wt. %, from 0.2 wt. % to 10 wt. % or from 0.25 wt. % to 5 wt. %. Preferably, the reaction is conducted under low water conditions and the reaction medium contains water in an amount from 0.1 to 4.1 wt. %, e.g., from 0.1 to 3.1 wt. % or from 0.5 to 2.8 wt. %. The concentration of methyl iodide in the reaction medium is maintained to be from 1 to 25 wt. %, e.g., from 5 to 20 wt. %, from 4 to 13.9 wt. %. The concentration of iodide salt, e.g., lithium iodide, in the reaction medium is maintained to be from 1 to 25 wt. %, e.g., from 2 to 20 wt. %, from 3 to 20 wt. %. The concentration of methyl acetate in the reaction medium is maintained to be from 0.5 to 30 wt. %, e.g., from 0.3 to 20 wt. %, from 0.6 to 9 wt. %, or from 0.6 to 4.1 wt. %. The following amounts are based on the total weight of the reaction medium.

The concentration of acetic acid in the reaction medium is generally greater than or equal to 30 wt. %, e.g., greater than or equal to 40 wt. % or greater than or equal to 50 wt. %.

In embodiments, the process for producing acetic acid further includes introducing a lithium compound into the reactor to maintain the concentration of lithium acetate in an amount from 0.3 to 0.7 wt. % in the reaction medium. In embodiments, an amount of the lithium compound is introduced into the reactor to maintain the concentration of hydrogen iodide in an amount from 0.1 to 1.3 wt. % in the reaction medium. In embodiments, the concentration of the rhodium catalyst is maintained in an amount from 200 to 3000 wppm in the reaction medium, the concentration of water is maintained in amount from 0.1 to 4.1 wt. % in the reaction medium, and the concentration of methyl acetate is maintained from 0.6 to 4.1 wt. % in the reaction medium, based on the total weight of the reaction medium present within the carbonylation reactor.

In embodiments, the lithium compound introduced into the reactor is selected from the group consisting of lithium acetate, lithium carboxylates, lithium carbonates, lithium hydroxide, other organic lithium salts, and mixtures thereof. In embodiments, the lithium compound is soluble in the reaction medium. In an embodiment, lithium acetate dihydrate may be used as the source of the lithium compound.

Lithium acetate reacts with hydrogen iodide according to the following equilibrium reaction (I) to form lithium iodide and acetic acid:

$$\text{LiOAc} + \text{HI} \rightleftharpoons \text{LiI} + \text{HOAc} \qquad (I)$$

Lithium acetate is thought to provide improved control of hydrogen iodide concentration relative to other acetates, such as methyl acetate, present in the reaction medium. Without being bound by theory, lithium acetate is a conjugate base of acetic acid and thus reactive toward hydrogen iodide via an acid-base reaction. This property is thought to result in an equilibrium of the reaction (I) which favors reaction products over and above that produced by the corresponding equilibrium of methyl acetate and hydrogen iodide. This improved equilibrium is favored by water concentrations of less than or equal to 4.1 wt. % in the reaction medium. In addition, the relatively low volatility of lithium acetate compared to methyl acetate allows the lithium acetate to remain in the reaction medium except for volatility losses and small amounts of entrainment into the vapor crude product. In contrast, the relatively high volatility of methyl acetate allows the material to distill into the purification train, rendering methyl acetate more difficult to control. Lithium acetate is much easier to maintain and control in the process at consistent low concentrations of hydrogen iodide. Accordingly, a relatively small amount of lithium acetate may be employed relative to the amount of methyl acetate needed to control hydrogen iodide concentrations in the reaction medium. It has further been discovered that lithium acetate is at least three times more effective than methyl acetate in promoting methyl iodide oxidative addition to the rhodium [I] complex.

In embodiments, the concentration of lithium acetate in the reaction medium is maintained at greater than or equal to 0.3 wt. %, or greater than or equal to 0.35 wt. %, or greater than or equal to 0.4 wt. %, or greater than or equal to 0.45 wt. %, or greater than or equal to 0.5 wt. %, and/or in embodiments, the concentration of lithium acetate in the reaction medium is maintained at less than or equal to 0.7 wt. %, or less than or equal to 0.65 wt. %, or less than or equal to 0.6 wt. %, or less than or equal to 0.55 wt. %.

It has been discovered that an excess of lithium acetate in the reaction medium can adversely affect the other compounds in the reaction medium, leading to decrease productivity. Conversely, it has been discovered that a lithium acetate concentration in the reaction medium below 0.3 wt. % results in a lack of control over hydrogen iodide concentrations within the reaction medium.

In embodiments, the lithium compound may be introduced continuously or intermittently into the reaction medium. In embodiments, the lithium compound is introduced during reactor start up. In embodiments, the lithium compound is introduced intermittently to replace entrainment losses.

In some embodiments, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously.

The carbonylation reaction of methanol to acetic acid product may be carried out by contacting the methanol feed with gaseous carbon monoxide bubbled through an acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion concentration is from 1 to 25 wt. % and the methyl acetate is generally present in amounts from 0.5 to 30 wt. %, and the methyl iodide is generally present in amounts from 1 to 25 wt. %. The rhodium catalyst is generally present in amounts from 200 to 3000 wppm.

The reaction medium may also contain impurities that should be controlled to avoid byproduct formation. One impurity in the reaction medium may be ethyl iodide, which is carbonylated to propionic acid. Applicant has further discovered that the formation of ethyl iodide may be affected by numerous variables, including the concentration of acetaldehyde, ethyl acetate, methyl acetate and methyl iodide in the reaction medium. Additionally, ethanol content in the methanol source, hydrogen partial pressure and hydrogen content in the carbon monoxide source have been discovered to affect ethyl iodide concentration in the reaction medium and, consequently, propionic acid concentration in the final acetic acid product.

In embodiments, the propionic acid concentration in the acetic acid product may further be maintained below 250 wppm by maintaining the ethyl iodide concentration in the reaction medium at less than or equal to 750 wppm without removing propionic acid from the acetic acid product.

In embodiments, the ethyl iodide concentration in the reaction medium and propionic acid in the acetic acid product may be present in a weight ratio from 3:1 to 1:2. In embodiments, the acetaldehyde:ethyl iodide concentration in the reaction medium is maintained at a weight ratio from 2:1 to 20:1.

In embodiments, the ethyl iodide concentration in the reaction medium may be maintained by controlling at least one of the hydrogen partial pressure, the methyl acetate concentration, the methyl iodide concentration, and/or the acetaldehyde concentration in the reaction medium.

In embodiments, the concentration of ethyl iodide in the reaction medium is maintained/controlled to be less than or equal to 750 wppm, or e.g., less than or equal to 650 wppm, or less than or equal to 550 wppm, or less than or equal to 450 wppm, or less than or equal to 350 wppm. In embodiments, the concentration of ethyl iodide in the reaction medium is maintained/controlled at greater than or equal to 1 wppm, or e.g., 5 wppm, or 10 wppm, or 20 wppm, or 25 wppm, and less than or equal to 650 wppm, or e.g., 550 wppm, or 450 wppm, or 350 wppm.

In embodiments, the weight ratio of ethyl iodide in the reaction medium to propionic acid in the acetic acid product may range from 3:1 to 1:2, or e.g., from 5:2 to 1:2, or from 2:1 to 1:2, or from 3:2 to 1:2.

In embodiments, the weight ratio of acetaldehyde to ethyl iodide in the reaction medium may range from 20:1 to 2:1, or e.g., from 15:1 to 2:1 or from 9:1 to 2:1.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. Gaseous purge stream 106 desirably is vented from the reactor 105 to prevent buildup of gaseous by-products and to maintain a set carbon monoxide partial pressure at a given total reactor pressure. In one embodiment, the gaseous purge stream 106 contains low amounts of hydrogen iodide of less than or equal to 1 wt. %, e.g., less than or equal to 0.9 wt. %, less than or equal to 0.8 wt. %, less than or equal to 0.7 wt. %, less than or equal to 0.5 wt. %. Hydrogen iodide in excess of these amounts may increase the duty on the scrubber to prevent hydrogen iodide from being purged. The temperature of the reactor may be controlled and the carbon monoxide feed is introduced at a rate sufficient to maintain the desired total reactor pressure. Stream 113 comprising the liquid reaction medium exits reactor 105.

The acetic acid production system preferably includes separation system 108 employed to recover the acetic acid and recycle metal catalyst, methyl iodide, methyl acetate, and other system components within the process. One or more of the recycle streams may be combined prior to being introduced into the reactor. The separation system also preferably controls water and acetic acid content in the carbonylation reactor, as well as throughout the system, and facilitates permanganate reducing compound ("PRC") removal. PRC's may include acetaldehyde, acetone, methyl ethyl ketone, butylaldehyde, crotonaldehyde, 2-ethyl crotonaldehyde, 2-ethyl butyraldehyde, and the aldol condensation products thereof. In one embodiment, a suitable potassium permanganate test is JIS K1351 (2007).

Flash Vessel

The reaction medium is drawn off from the carbonylation reactor 105 at a rate sufficient to maintain a constant level therein and is provided to flash vessel 110 via stream 113. The flash separation may be carried out at a temperature from 80° C. to 200° C., under an absolute pressure from 1 to 10 atm. In flash vessel 110, the reaction medium is separated in a flash separation step to obtain a vapor product stream 112 comprising acetic acid and liquid recycle 111 comprising a catalyst-containing solution. The respective flow rates of vapor product stream 112 and liquid recycle 111 may vary, and in one exemplary embodiment 15% to 55% of the flow into flash vessel 110 is removed as vapor product stream 112 and 45% to 85% of the flow is removed as liquid recycle 111. The catalyst-containing solution may be predominantly acetic acid containing the rhodium and the iodide salt along with lesser quantities of methyl acetate, methyl iodide, and water and is recycled to the reactor, as discussed above. Prior to returning liquid recycle to the reactor, a slip stream may pass through a corrosion metal removal bed, such as an ion exchange bed, to remove any entrained corrosion metals, such as nickel, iron, chromium, and molybdenum, as described in U.S. Pat. No. 5,731,252, which is incorporated herein by reference in their entirety. Also, the corrosion metal removal bed may be used to remove nitrogen compounds, such as amines, as described in U.S. Pat. No. 8,697,908, which is incorporated herein by reference in their entirety.

In one embodiment, vapor product stream 112 comprises acetic acid, methyl iodide, methyl acetate, water, acetaldehyde, and hydrogen iodide. In one embodiment, vapor product stream 112 comprises acetic acid in an amount from 45 to 75 wt. %, methyl iodide in an amount from 20 to 50 wt. %, methyl acetate in an amount of less than or equal to 9 wt. %, and water in an amount of less than or equal to 15 wt. %, based on the total weight of the vapor product stream. In another embodiment, vapor product stream 112 comprises acetic acid in an amount from 45 to 75 wt. %, methyl iodide in an amount from 24 to less than or equal to 36 wt. %, methyl acetate in an amount of less than or equal to 9 wt. %, and water in an amount of less than or equal to 15 wt. %, based on the total weight of the vapor product stream. More preferably, vapor product stream 112 comprises acetic acid in an amount from 55 to 75 wt. %, methyl iodide in an amount from 24 to 35 wt. %, methyl acetate in an amount from 0.5 to 8 wt. %, and water in an amount from 0.5 to 14 wt. %. In yet a further preferred embodiment, vapor product stream 112 comprises acetic acid in an amount from 60 to 70 wt. %, methyl iodide in an amount from 25 to 35 wt. %, methyl acetate in an amount from 0.5 to 6.5 wt. %, and water in an amount from 1 to 8 wt. %. The acetaldehyde concentration in the vapor product stream may be in an amount from 0.005 to 1 wt. %, based on the total weight of the vapor product stream, e.g., from 0.01 to 0.8 wt. %, or from 0.01 to 0.7 wt. %. In some embodiments the acetaldehyde may be present in amounts less than or equal to 0.01 wt. %. Vapor product stream 112 may comprise hydrogen iodide in an amount less than or equal to 1 wt. %, based on the total weight of the vapor product stream, e.g., less than or equal to 0.5 wt. %, or less than or equal to 0.1 wt. %. Vapor product stream 112 is preferably substantially free of, i.e., contains less than or equal to 0.0001 wt. %, propionic acid, based on the total weight of the vapor product stream.

Liquid recycle stream 111 comprises acetic acid, the metal catalyst, corrosion metals, as well as other various compounds. In one embodiment, liquid recycle stream comprises acetic acid in an amount from 60 to 90 wt. %, metal catalyst in an amount from 0.01 to 0.5 wt. %, corrosion metals (e.g., nickel, iron and chromium) in a total amount from 10 to 2500 wppm, lithium iodide in an amount from 5 to 20 wt. %, methyl iodide in an amount from 0.5 to 5 wt. %, methyl acetate in an amount from 0.1 to 5 wt. %, water in an amount from 0.1 to 8 wt. %, acetaldehyde in an amount of less than or equal to 1 wt. % (e.g., from 0.0001 to 1 wt. % acetaldehyde), and hydrogen iodide in an amount of less than or equal to 0.5 wt. % (e.g., from 0.0001 to 0.5 wt. % hydrogen iodide).

In addition to acetic acid, vapor product stream 112 also comprises methyl iodide, methyl acetate, water, and PRC's, e.g., acetaldehyde and crotonaldehyde. Dissolved gases exiting reactor 105 and entering flash vessel 110 comprise a portion of the carbon monoxide and may also contain gaseous by-products such as methane, hydrogen, and carbon dioxide. Such dissolved gases exit flash vessel 110 as part of the vapor product stream 112. In one embodiment, carbon monoxide in gaseous purge stream 106 may be fed to the base of flash vessel 110 to enhance rhodium stability.

Recovery of Acetic Acid

The distillation and recovery of acetic acid is not particularly limited for the purposes of the present invention.

First Column

As shown in FIG. 1, vapor product stream 112 is directed to a first column 120, also referred to as a light ends column. In one embodiment, vapor product stream 112 may comprise acetic acid, methyl acetate, water, methyl iodide, and acetaldehyde, along with other impurities such as hydrogen iodide and crotonaldehyde, and byproducts such as propionic acid. Distillation yields a low-boiling overhead vapor stream 122, a purified acetic acid product that preferably is removed via a side stream 123, and a high boiling residue stream 121. A majority of the acetic acid is removed in side stream 123 and preferably little or no acetic acid is recovered from high boiling residue stream 121. Although the concentration of acetic acid may be relatively high in boiling residue stream 121, the mass flow of the boiling residue stream 121 relative to side stream 123 is very small. In embodiments, the mass flow of the boiling residue stream 121 is less than or equal to 0.75% of side stream 123, e.g., less than or equal to 0.55%, or less than or equal to 0.45%.

In one embodiment, low-boiling overhead vapor stream 122 comprises water in amount greater than or equal to 5 wt. %, e.g., greater than or equal to 10 wt. %, or greater than or equal to 25 wt. %. The amount of water may be up to 80 wt. %. In terms of ranges, water concentration in the overhead may be from 5 wt. % to 80 wt. %, e.g., from 10 wt. % to 70 wt. % or from 25 wt. % to 60 wt. %. Reducing water concentration to less than 5 wt. % is not advantageous because this results in a large recycle of acetic acid back to the reaction system which then sets up a large recycle through the entire purification system. In addition to water, low-boiling overhead vapor stream 122 may also comprise methyl acetate, methyl iodide, and carbonyl impurities, which are preferably concentrated in the overhead to be removed from acetic acid in side stream 123. These carbonyl impurities may also be referred to herein as PRC's.

As shown, low-boiling overhead vapor stream 122 preferably is condensed and directed to an overhead phase separation unit, as shown by overhead decanter 124. Conditions are desirably maintained such that the condensed low-boiling overhead vapor stream 122, once in decanter 124, may separate to form a light liquid phase 133 and a heavy liquid phase 134. The phase separation should maintain two separate phases, without forming a third phase or emulsion between the phases. An offgas component may be vented via line 132 from decanter 124. In embodiments, the average residence time of the condensed low-boiling overhead vapor stream 122 in overhead decanter 124 is greater than or equal to 1 minute, e.g., greater than or equal to 3 minutes, greater than or equal to 5 minutes, greater than or equal to 10 minutes, and/or the average residence time is less than or equal to 60 minutes, e.g., less than or equal to 45 minutes, or less than or equal to 30 minutes, or less than or equal to 25 minutes.

Although the specific compositions of light liquid phase 133 may vary widely, some exemplary compositions are provided below in Table 1.

TABLE 1

Exemplary Light Liquid Phase from Light Ends Overhead

| | conc. (Wt. %) | conc. (Wt. %) | conc. (Wt. %) |
|---|---|---|---|
| Water | 40-80 | 50-75 | 70-75 |
| Methyl Acetate | 1-50 | 1-25 | 1-15 |
| Acetic Acid | 1-40 | 1-25 | 5-15 |
| PRC's (AcH) | <5 | <3 | <1 |
| Methyl Iodide | <10 | <5 | <3 |
| Hydrogen Iodide | <1 | <0.5 | 0.001-0.5 |

In one embodiment, overhead decanter 124 is arranged and constructed to maintain a low interface level to prevent an excess hold up of methyl iodide. Although the specific compositions of heavy liquid phase 134 may vary widely, some exemplary compositions are provided below in Table 2.

TABLE 2

Exemplary Heavy Liquid Phase from Light Ends Overhead

|  | conc. (Wt. %) | conc. (Wt. %) | conc. (Wt. %) |
|---|---|---|---|
| Water | <3 | 0.05-1 | 0.01-1 |
| Methyl Acetate | 0.1-25 | 0.5-20 | 0.7-15 |
| Acetic Acid | 0.1-10 | 0.5-10 | 0.7-10 |
| PRC's (AcH) | <5 | <3 | 0.05-0.5 |
| Methyl Iodide | 60-98 | 60-95 | 80-90 |
| Hydrogen Iodide | <1 | <0.5 | 0.001-0.5 |

The density of the heavy liquid phase 134 may be from 1.3 to 2, e.g., from 1.5 to 1.8, from 1.5 to 1.75 or from 1.55 to 1.7. As described in U.S. Pat. No. 6,677,480, the measured density in the heavy liquid phase 134 may correlate to the methyl acetate concentration in the reaction medium. As density decreases, the methyl acetate concentration in the reaction medium increases. In one embodiment of the present invention, heavy liquid phase 134 is recycled to the reactor and the light liquid phase 133 is controlled to be recycled through the same pump. It may be desirable to recycle a portion of the light liquid phase 133 that does not disrupt the pump and maintains a density of the combined light liquid phase 133 and heavy liquid phase of greater than or equal to 1.3, e.g., greater than or equal to 1.4, greater than or equal to 1.5, or greater than or equal to 1.7. As described herein, a portion of the heavy liquid phase 134 may be treated to remove impurities such as acetaldehyde.

As indicated by Tables 1 and 2, the water concentration in the light liquid phase 133 is larger than the heavy liquid phase 134 and thus the present invention can control the side stream water concentration through the recycle of the light liquid phase. The concentration of water and hydrogen iodide is controlled in side stream 123 by the recycle rate of light liquid phase 133 to reactor 105 via line 136. The reflux ratio (meaning herein as the mass flow rate of the reflux divided by the total mass flow exiting the top of the column 120, including both heavy phase 134 which may be fully recycled and light phase 133) to the first column of the light liquid phase 133 via line 135 preferably is from 0.05 to 0.4, e.g., from 0.1 to 0.35 or from 0.15 to 0.3. In one embodiment, to reduce the reflux ratio, the number of theoretical trays above the side stream and top of first column may be greater than or equal to 5, e.g., preferably greater than or equal to 10. In another embodiment, the recycle of light liquid phase in line 136 back to reactor 105 is up to or equal to 20%, e.g., up to or equal to 10%, of the total light liquid phase 133 condensed from the column overhead (reflux plus recycle). In terms of ranges the recycle of light liquid phase in line 136 may be from 0 to 20% e.g., from 0.1 to 20%, from 0.5 to 20%, from 1 to 15%, or from 1 to 10%, of the total light liquid phase 133 condensed from the low boiling overhead vapor stream (reflux plus recycle). The remaining portion may be used as a reflux on the light ends column or fed to an acetaldehyde reduction system. As shown in FIG. 1, recycle in line 136 may be combined with liquid recycle 111 and indirectly returned to reactor 105. In one embodiment, recycle in line 136 may be combined with another stream that is being recycled to indirectly recycle to reactor 105 or may be recycled directly to reactor 105. When condensed overhead stream 138 from drying column 125 is phased to form aqueous phase and an organic phase, the recycle in line 136 may be preferably combined with aqueous phase. Alternatively, recycle in line 136 may be combined, or at least partially combined, with heavy 134 and/or the organic phase from the overhead stream 138.

In an embodiment of the present invention, there is provided a process for producing acetic acid comprising separating a reaction medium formed in a reactor in a flash vessel to form a liquid recycle and a vapor product stream, distilling the vapor product stream in a first column to obtain a side stream and a low boiling overhead vapor stream comprising water in an amount of greater than or equal to 5 wt. %, condensing the low boiling overhead vapor stream and biphasically separating the condensed stream to form a heavy liquid phase and a light liquid phase, maintaining a recycle 0.5% to 20% of the light liquid phase, based on the total light phase 133 condensed from the column overhead, to the reactor to maintain a water concentration in the side stream in an amount from 1 to 3 wt. %, and hydrogen iodide in amount of less than or equal to 50 wppm hydrogen iodide, and distilling the side stream in a second column to obtain a purified acetic acid product.

For purposes of the present invention, a flow valve (not shown) and/or flow monitor (not shown) may be used to control the reflux in line 135 and recycle in line 136. In one embodiment, hydrogen iodide concentration in side stream 123 may be determined by feeding a sample stream 141 to an on-line analyzer 142. In one embodiment, the controls for the reflux in line 135 and recycle in line 136 may be in communication with on-line analyzer 142 that may provide feedback information to control the respective reflux ratio and recycle to reactor. Changing the reflux ratio may impact the amount of water that is recycled to the reactor. In some embodiments, the amount may be changed so that there is no recycle of the light liquid phase 133 to the reactor. Reducing the reflux (and increasing the recycle to the reactor) decreases the side stream water content. Increasing the reflux increases the water concentration in side stream and decreases the water recycled to the reactor. Increasing the reflux ratio above 0.4 increases the water concentration above 3 wt. % in side stream, which makes separation in the second column difficult for removing water, methyl acetate, and methyl iodide from the acetic acid. Thus, the acetic acid withdrawn from the drying column, either in the bottoms or side near the bottom, may contain a total iodide concentration that is too high for efficient handling by guard beds.

PRC Removal System

Although not shown a portion of light liquid phase 133 and/or heavy liquid phase 134 may be separated and directed to acetaldehyde or PRC removal system to recover methyl iodide and methyl acetate during the acetaldehyde removal process. As shown in Tables 1 and 2, light liquid phase 133 and/or heavy liquid phase 134 each contain PRC's and the process may include removing carbonyl impurities, such as acetaldehyde, that deteriorate the quality of the acetic acid product and may be removed in suitable impurity removal columns and absorbers as described in U.S. Pat. Nos. 6,143,930; 6,339,171; 7,223,883; 7,223,886; 7,855,306; 7,884,237; 8,889,904; and US Pub. Nos. 2006/0011462, which are incorporated herein by reference in their entirety. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from the liquid light phase.

The portion of light liquid phase 133 and/or heavy liquid phase 134 fed to the acetaldehyde or PRC removal system may vary from 1% to 99% of the mass flow of either the light liquid phase 133 and/or heavy liquid phase 134, e.g., from 1 to 50%, from 2 to 45%, from 5 to 40%, 5 to 30% or 5 to 20%. Also in some embodiments, a portion of both the light liquid phase 133 and heavy liquid phase 134 may be fed to the acetaldehyde or PRC removal system. The portion of the light liquid phase 133 not fed to the acetaldehyde or PRC removal system may be refluxed to the first column or recycled to the reactor, as described herein. The portion of the heavy liquid phase 134 not fed to the acetaldehyde or PRC removal system may be recycled to the reactor. Although a portion of heavy liquid phase 134 may be refluxed to the first column, it is more desirable to return the methyl iodide enriched heavy liquid phase 134 to the reactor.

In one embodiment, a portion of light liquid phase 133 and/or heavy liquid phase 134 is fed to a distillation column which enriches the overhead thereof to have acetaldehyde and methyl iodide. Depending on the configuration, there may be two separate distillation columns, and the overhead of the second column may be enriched in acetaldehyde and methyl iodide. Dimethyl ether, which may be formed in-situ, may also be present in the overhead. The overhead may be subject to one or more extraction stages to remove a raffinate enriched in methyl iodide and an extractant. A portion of the raffinate may be returned to the distillation column, first column, overhead decanter and/or reactor. For example, when the heavy liquid phase 134 is treated in the PRC removal system, it may be desirable to return a portion the raffinate to either the distillation column or reactor. Also, for example, when light liquid phase 133 is treated in the PRC removal system, it may be desirable to return a portion the raffinate to either the first column, overhead decanter, or reactor. In some embodiments, the extractant may be further distilled to remove water, which is returned to the one or more extraction stages. The bottoms, which contains more methyl acetate and methyl iodide than light liquid phase 133, may also be recycled to reactor 105 and/or refluxed to first column 120.

In one embodiment, there is provided a process for producing acetic acid comprising separating a reaction medium formed in a reactor in a flash vessel to form a liquid recycle and a vapor product stream, distilling the vapor product stream in a first column to obtain a side stream and a low boiling overhead vapor stream comprising water in an amount of greater than or equal to 5 wt. %, condensing the low boiling overhead vapor stream and biphasically separating the condensed stream to form a heavy liquid phase and a light liquid phase, separating a portion of the heavy liquid phase to remove acetaldehyde or other PRC's, maintaining a water concentration in the side stream from 1 to 3 wt. %, e.g., preferably from 1.1 to 2.5 wt. %, and a hydrogen iodide concentration in the side stream in an amount of less than or equal to 50 wppm, e.g., preferably from 0.1 to 50 wppm, by controlling a recycle rate of the light liquid phase to the reactor, and distilling the side stream in a second column to obtain a purified acetic acid product.

Under low water conditions in the reactor, there is provided a process for producing acetic acid comprising separating a reaction medium formed in a reactor in a flash vessel to form a liquid recycle and a vapor product stream, wherein the reaction medium comprises water in an amount from 0.1 to 4.1 wt. %, distilling a portion of the vapor product stream in a first column to obtain a side stream, a low boiling overhead vapor stream comprising water in an amount of greater than or equal to 5 wt. %, and a residuum stream comprising acetic acid in an amount greater than or equal to 95 wt. % and water in an amount less than or equal to 5 wt. %, condensing the low boiling overhead vapor stream and biphasically separating the condensed stream to form a heavy liquid phase and a light liquid phase, separating a portion of the heavy liquid phase to remove acetaldehyde or other PRC's, maintaining a water concentration in the side stream from 1 to 3 wt. %, e.g., preferably from 1.1 to 2.5 wt. %, and a hydrogen iodide concentration in the side stream in an amount of less than or equal to 50 wppm, e.g., preferably from 0.1 to 50 wppm, by controlling a recycle rate of the light liquid phase to the reactor, and distilling the side stream in a second column to obtain a purified acetic acid product.

Second Column

Acetic acid removed via side stream 123 preferably is subjected to further purification, such as in a second column 125, also referred to as a drying column, and separates side stream 123 to form aqueous overhead stream 126 comprised primarily of water and product stream 127 comprised primarily of acetic acid. Water from the side stream is concentrated in the aqueous overhead stream and the aqueous overhead comprises greater than or equal to 90% of the water in the side stream fed to the second column, e.g., greater than or equal to 95%, greater than or equal to 97%, greater than or equal to 99%. Aqueous overhead stream 126 may comprise water in an amount from 50 to 75 wt. %. In embodiments, aqueous overhead stream may comprise water in an amount of less than or equal to 75 wt. %, e.g., less than or equal to 70 wt. %, less than or equal to 65 wt. %. Methyl acetate and methyl iodide are also removed from the side stream and concentrated in the overhead stream. Product stream 127 preferably comprises or consists essentially of acetic acid and may be withdrawn in the bottom of second column 125 or a side stream near the bottom. When withdrawn as a side stream near the bottom, the side stream may be a liquid or a vapor stream. In preferred embodiments, product stream 127 comprises acetic acid in an amount greater than or equal to 90 wt. %, e.g., greater than or equal to 95 wt. % or greater than or equal to 98 wt. %. Product stream 127 may be further processed, e.g., by passing through an ion exchange resin, prior to being stored or transported for commercial use.

Similarly, aqueous overhead stream 126 from second column 125 contains a reaction component, such as methyl iodide, methyl acetate, and water, and it is preferable to retain these reaction components within the process. Aqueous overhead stream 126 is condensed by a heat exchanger into stream 138, which is recycled to reactor 105 and/or refluxed second column 125. An offgas component may be vented via line 137 from condensed low-boiling overhead vapor stream 126. Similar to the condensed low-boiling overhead vapor stream from first column 120, condensed overhead stream 138 may also be separated to form an aqueous phase and an organic phase, and these phases may be recycled or refluxed as needed to maintain the concentrations in the reaction medium.

In one embodiment, the side stream water concentration is controlled to balance the water in both the first and second columns. When less than or equal to 14 wt. % is used in the reaction medium, more preferably, less than or equal to 4.1 wt. % there may not be sufficient water in the second column to stably operate the column. Although it may be possible to reduce the water concentration in the side stream to less than or equal to 1 wt. %, this would result in an imbalance in the second column which may cause the recovery of acetic acid to become more difficult and result in off-spec product. Further, by having water in the side stream the second column is able to remove that water in the aqueous overhead. The recycle ratio between the light liquid phase from the first column and the aqueous overhead from the second column helps to maintain desirable water concentrations in the reactor while maintaining stable operations in the first and second distillation columns. In one embodiment, the recycle ratio of the mass flow of the light liquid phase recycled to the reactor to the mass flow of the aqueous overhead to the reactor is less than or equal to 2, e.g., less than or equal to 1.8, less than or equal to 1.5, less than or equal to 1, less than or equal to 0.7, less than or equal to 0.5, less than or equal to 0.35, less than or equal to 0.25 and/or the recycle ratio of the mass flow of the light liquid phase recycled to the reactor to the mass flow of the aqueous overhead to the reactor is greater than or equal to 0, e.g., greater than or equal to 0.05, greater than or equal to 0.1, greater than or equal to 0.15, or greater than or equal to 0.2. In one embodiment, the recycle ratio of the mass flow of the light liquid phase recycled to the reactor to the mass flow of the aqueous overhead to the reactor is from 0 to 2, e.g., from 0 to 1.5, from 0 to 1.3, from 0 to 1, from 0 to 0.9 from 0 to 0.7, from 0 to 0.5, from 0 to 0.35 or from 0 to 0.25. Thus, in one embodiment, there is provided a process for producing acetic acid comprising separating a reaction medium formed in a reactor in a flash vessel to form a liquid recycle and a vapor product stream, distilling the vapor product stream in a first column to obtain a side stream and a first low boiling overhead vapor stream, wherein the side stream comprises water in an amount from 1 to 3 wt. %, condensing the first low boiling overhead vapor stream and biphasically separating the condensed stream to form a heavy liquid phase and a light liquid phase, distilling the side stream in a second column to obtain a purified acetic acid product and a second low boiling overhead vapor stream, condensing the second low boiling overhead vapor stream to obtain an aqueous recycle stream, comprising water in an amount of less than or equal to 75 wt. %, and recycling the second low boiling overhead vapor stream to the reactor, wherein the recycle ratio of the mass flow of the light liquid phase recycled to the reactor to the mass flow of the aqueous recycle stream to the reactor is less than or equal to 2, e.g., from 0 to 2.

To recover residue liquids from the vent streams, in particular lines 106, 132, and 137, these lines may be fed to a scrubber that operates with chilled methanol and/or acetic acid to remove methyl acetate and methyl iodide. A suitable scrubber is described in U.S. Pat. No. 8,318,977, which is incorporated herein by reference in its entirety.

The distillation columns of the present invention may be a conventional distillation column, e.g., a plate column, a packed column, and others. Plate columns may include a perforated plate column, bubble-cap column, Kittel tray column, uniflux tray, or a ripple tray column. For a plate column, the theoretical number of plates is not particularly limited and depending on the species of the component to be separate, may include up to 80 plates, e.g., from 2 to 80, from 5 to 60, from 5 to 50, or more preferably from 7 to 35. The distillation column may include a combination of different distillation apparatuses. For example, a combination of bubble-cap column and perforated plate column may be used as well as a combination of perforated plate column and a packed column.

The distillation temperature and pressure in the distillation system can suitably be selected depending on the condition such as the species of the objective carboxylic acid and the species of the distillation column, or the removal target selected from the lower boiling point impurity and the higher boiling point impurity according to the composition of the feed stream. For example, in a case where the purification of acetic acid is carried out by the distillation column, the inner pressure of the distillation column (usually, the pressure of the column top) may be from 0.01 to 1 MPa, e.g., from 0.02 to 0.7 MPa, and more preferably from 0.05 to 0.5 MPa in terms of gauge pressure. Moreover, the distillation temperature for the distillation column, namely the inner temperature of the column at the temperature of the column top, can be controlled by adjusting the inner pressure of the column, and, for example, may be from 20 to 200° C., e.g., from 50 to 180° C., and more preferably from 100 to 160° C.

The material of each member or unit associated with the distillation system, including the columns, valves, condensers, receivers, pumps, reboilers, and internals, and various lines, each communicating to the distillation system may be made of suitable materials such as glass, metal, ceramic, or combinations thereof, and is not particularly limited to a specific one. According to the present invention, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloys include those containing iron as a main component, e.g., a stainless steel that also comprises chromium, nickel, molybdenum and others. Suitable alloys include those containing nickel as a main component and one or more of chromium, iron, cobalt, molybdenum, tungsten, manganese, and others, e.g., HASTELLOY™ and INCONEL™. Corrosion-resistant metals may be particularly suitable as materials for the distillation system and various lines.

Guard Bed

Carboxylic acid streams, e.g., acetic acid streams, that are contaminated with a halides and/or corrosion metals may be contacted with an ion exchange resin composition under a wide range of operating conditions. Preferably, the ion exchange resin composition is provided in a guard bed. The use of guard beds to purify contaminated carboxylic acid streams is well documented in the art, for example, U.S. Pat. Nos. 4,615,806; 5,653,853; 5,731,252; and 6,225,498, which are hereby incorporated by reference in their entireties. Generally, a contaminated liquid carboxylic acid stream is contacted with an ion exchange resin composition, which is preferably disposed in the guard bed. The halide contaminants, e.g., iodide contaminants, react with the metal to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

In one embodiment, the ion exchange resin is a metal-exchanged ion exchange resin and may comprise at least one metal selected from the group consisting of silver, mercury, palladium and rhodium. In one embodiment, at least 1% of the strong acid exchange sites of said metal-exchanged resin are occupied by silver. In another embodiment, at least 1% of the strong acid exchange sites of said metal-exchanged resin are occupied by mercury. The process may further comprise treating the purified acetic acid product with a cationic exchange resin to recover any silver, mercury, palladium or rhodium.

The pressure during the contacting step is limited only by the physical strength of the resin. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) to 118° C. (the boiling point of acetic acid). It is within the purview of those skilled in the art to determine analogous ranges for product streams comprising other carboxylic acid compounds. The temperature of the contacting step preferably is kept relatively low to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin degrading (via the mechanism of acid-catalyzed aromatic desulfonation) at temperatures of 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for halide removal.

The configuration of the guard bed within an acetic acid purification train may vary widely. For example, the guard bed may be configured after a drying column. Additionally or alternatively, the guard be may be configured after a heavy ends removal column or finishing column. Preferably the guard bed is configured in a position wherein the temperature acetic acid product stream is low, e.g., less than or equal to 120° C. or less than or equal to 100° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

In one embodiment, the flow rate through the guard bed ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

To avoid exhausting the resin with a purified acetic acid product that is high in total iodide concentration, in one embodiment the purified acetic acid product in bottoms stream 127 is contacted with a guard bed when total iodide concentration of the purified acetic acid product is less than or equal to 5 wppm, e.g., preferably less than or equal to 1 wppm. Total iodide concentration includes iodide from both organic, $C_1$ to $C_{14}$ alkyl iodides, and inorganic sources, such as hydrogen iodide. A purified acetic acid composition is obtained as a result of the guard bed treatment. The purified acetic acid composition, in one embodiment, comprises less than or equal to 100 wppb iodides, e.g., less than or equal to 90 wppb, less than or equal to 50 wppb, or less than or equal to 25 wppb. In one embodiment, the purified acetic acid composition comprises less than or equal to 1000 wppb corrosion metals, e.g., less than or equal to 750 wppb, less than or equal to 500 wppb, or less than or equal to 250 wppb. For purposes of the present invention, corrosion metals include metals selected from the group consisting of nickel, iron, chromium, molybdenum and combinations thereof. In terms of ranges, the purified acetic acid composition may comprise from 0 to 100 wppb iodides, e.g., from 1 to 50 wppb, and/or from 0 to 1000 wppb corrosion metals, e.g., from 1 to 500 wppb. In other embodiments, the guard bed removes at least 25 wt. % of the iodides from the crude acetic acid product, e.g., at least 50 wt. % or at least 75 wt. %. In one embodiment, the guard bed removes at least 25 wt. % of the corrosion metals from the crude acetic acid product, e.g., at least 50 wt. % or at least 75 wt. %.

In another embodiment, the product stream may be contacted with cationic exchanger to remove lithium compounds. The cationic exchanger in the acid form comprises a resin of acid-form strong acid cation exchange macroreticular, macroporous or mesoporous resins. Without being bound by theory feeding a product stream to an ion-exchange comprises lithium compounds in an amount of greater than or equal to 10 wppm results in displacement of metals in the treated product. Advantageously, this may be overcome by using an cationic exchanger upstream of the ion-exchange resin. After contacting with the cationic exchanger, the product stream may have a lithium ion concentration of less than or equal to 50 weight part per billion (wppb), e.g., less than or equal to 10 wppb, or less than or equal to 5 wppb.

Although the product stream may be contacted with an ion-exchange resin to remove iodides, it is preferred not to flash the product stream or contact with product stream with an adsorption system that contains activated carbon. Flashing the product stream is not efficient because there is not a sufficient pressure drop to recover greater than 50% of the acetic acid from the product stream. Thus, in one embodiment, a non-flashed portion of the product stream is fed to the ion-exchange bed to remove iodides.

As is evident from the figures and text presented above, a variety of embodiments are contemplated.

E1. A process for producing acetic acid comprising:
separating a reaction medium formed in a reactor in a flash vessel to form a liquid recycle and a vapor product stream;
distilling the vapor product stream in a first column to obtain a side stream and a low boiling overhead vapor stream comprising water in an amount of greater than or equal to 5 wt. %;
condensing the low boiling overhead vapor stream and biphasically separating the condensed stream to form a heavy liquid phase and a light liquid phase;
maintaining a water concentration in the side stream from 1 to 3 wt. % and a hydrogen iodide concentration in the side stream in an amount of less than or equal to 50 wppm, based on the total weight of the side stream, by controlling a recycle rate of the light liquid phase to the reactor; and
distilling the side stream in a second column to obtain a purified acetic acid product.

E2. A process for producing acetic acid comprising:
separating a reaction medium formed in a reactor in a flash vessel to form a liquid recycle and a vapor product stream, wherein the reaction medium comprises water in an amount from 0.1 to 4.1 wt. %;
distilling a portion of the vapor product stream in a first column to obtain a side stream, a low boiling overhead vapor stream comprising water in an amount of greater than or equal to 5 wt. %, and a residuum stream comprising acetic acid in an amount greater than or equal to 95 wt. % and water in an amount less than or equal to 5 wt. %;
condensing the low boiling overhead vapor stream and biphasically separating the condensed stream to form a heavy liquid phase and a light liquid phase;
maintaining a water concentration in the side stream from 1 to 3 wt. % and a hydrogen iodide concentration in the side stream of less than or equal to 50 wppm, based on the total weight of the side stream, by controlling a recycle rate of a portion of the light liquid phase to the reactor; and
distilling the side stream in a second column to obtain a purified acetic acid product.

E3. The process of any of embodiments E1-E2, wherein the reaction medium further comprises methyl acetate, a metal catalyst, an iodide salt and methyl iodide.

E4. The process of any of embodiments E1-E3, wherein the reaction medium comprises methyl acetate in an amount from 0.5 to 30 wt. %, a metal catalyst in an amount from 200 to 3000 wppm, iodide salt in an amount from 1 to 25 wt. %, and methyl iodide in an amount from 1 to 25 wt. %.

E5. The process of any of embodiments E1-E4, wherein a portion of the heavy liquid phase is treated to remove at least one permanganate reducing compound selected from the group consisting of acetaldehyde, acetone, methyl ethyl ketone, butylaldehyde, crotonaldehyde, 2-ethyl crotonaldehyde, 2-ethyl butyraldehyde, and the aldol condensation products thereof.

E6. The process of any of embodiments E1-E5, wherein the water concentration is maintained in the side stream from 1.1 to 2.5 wt. %.

E7. The process of any of embodiments E1-E6, wherein the hydrogen iodide concentration is maintained in the side stream from 0.1 to 50 wppm.

E8. The process of any of embodiments E1-E7, wherein the side stream further comprises one or more C1-C14 alkyl iodides in an concentration from 0.1 to 6 wt. % and the side stream further comprises methyl acetate in an concentration from 0.1 to 6 wt. %.

E9. The process of any of embodiments E1-E8, wherein the side stream comprises each of the one or more C1-C14 alkyl iodides and the methyl acetate in an amount ±0.9 wt. % of the water concentration in the side stream.

E10. The process of any of embodiments E1-E9, wherein the first column is operated with a reflux ratio from 0.05 to 0.4.

E11. The process of any of embodiments E1-E10, further comprising refluxing the heavy liquid phase, the light liquid phase, or a mixture thereof to the first column.

E12. The process of any of embodiments E1-E11, wherein the light liquid phase comprises water in an amount from 40 to 80 wt. %.

E13. The process of any of embodiments E1-E12, wherein the heavy liquid phase comprises water in an amount of less than or equal to 1 wt. %.

E14. The process of any of embodiments E1-E13, wherein the purified acetic acid product is withdrawn from the bottoms or near the bottoms of the second column.

E15. The process of any of embodiments E1-E14, wherein an aqueous overhead is withdrawn from the second column.

E16. The process of any of embodiments E1-E15, wherein the aqueous overhead comprises greater than or equal to 90% of the water in the side stream fed to the second column.

E17. The process of any of embodiments E1-E16, further comprising recycling the aqueous overhead, or a condensed portion thereof, to the reactor, wherein the recycle ratio of the mass flow of the light liquid phase recycled to the reactor to the mass flow of the aqueous overhead to the reactor is less than or equal to 2.

E18. The process of any of embodiments E1-E17, wherein water, methyl acetate, or a combination thereof is not introduced to the vapor stream.

E19. The process of any of embodiments E1-E18, wherein water, methyl acetate, or a combination thereof is not introduced to the first stream.

E20. The process of any of embodiments E1-E19, further comprising contacting the purified acetic acid product with a guard bed when total iodide concentration of the purified acetic acid product is less than or equal to 5 wppm.

E21. The process of any of embodiments E1-E20, wherein the recycle of light liquid phase is from 0 to 20%, of the total light phase condensed from the low boiling overhead vapor stream.

E22. The process of any of embodiments E1-E20, further comprising controlling an ethyl iodide concentration in the reaction medium at less than or equal to 750 wppm, and wherein the acetic acid product comprises less than 250 wppm propionic acid without directly removing propionic acid from the acetic acid product.

E23. The process of embodiment E22, wherein ethyl iodide in the reaction medium and propionic acid in the acetic acid product are present in a weight ratio from 3:1 to 1:2.

E24. The process of embodiment E22, wherein acetaldehyde and ethyl iodide are present in the reaction medium in a weight ratio from 2:1 to 20:1.

E25. A process for producing acetic acid comprising:
 separating a reaction medium formed in a reactor in a flash vessel to form a liquid recycle and a vapor product stream;
 distilling the vapor product stream in a first column to obtain a side stream and a low boiling overhead vapor stream;
 condensing the low boiling overhead vapor stream and biphasically separating the condensed stream to form a heavy liquid phase and a light liquid phase;
 measuring hydrogen iodide concentration in the side stream;
 controlling recycle rate of the light liquid phase to the reactor in response to the measured hydrogen iodide to maintain hydrogen iodide concentration in the side stream of less than or equal to 50 wppm; and
 distilling the side stream in a second column to obtain a purified acetic acid product.

E26. The process of embodiment E25, wherein the hydrogen iodide concentration in the side stream is measured by potentiometric titration using lithium acetate as the titrant.

E27. A process for producing acetic acid comprising:
 separating a reaction medium formed in a reactor in a flash vessel to form a liquid recycle and a vapor product stream;
 distilling the vapor product stream in a first column to obtain a low boiling overhead vapor stream and a side stream comprising water in an amount from 1 to 3 wt. %, one or more C1-C14 alkyl iodides in an amount from 0.1 to 6 wt. %, and hydrogen iodide in an amount of less than or equal to 50 wppm;
 distilling the side stream in a second column to obtain a purified acetic acid product; and contacting the purified acetic acid product with a guard bed when total iodide concentration of the purified acetic acid product is less than or equal to 5 wppm.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

EXAMPLES

The present invention will be better understood in view of the following non-limiting examples.

Comparative Example 1

No Light Phase Recycle

A typical example of the HI concentration in side stream was determined by titrating 0.2 g of side stream sample with 0.01 M lithium acetate solution in 50 ml acetone. A pH electrode was used with Metrohm 716 DMS Titrino to determine the end point at Dynamic Equivalence-point Titration mode. HI concentration in wt. % was calculated based on the consumption of lithium acetate titrant as depicted in following equation.

$$HI \text{ } wt. \text{ } \% = \frac{(\text{ml of } LiOAc)(0.01M)(\text{mole}/l)(128 \text{ g/mole}) \times 100}{(\text{g sample})(1000 \text{ ml}/l)}$$

A sample side stream composition having about 1.9 wt. % water, about 2.8 wt. % methyl iodide, and about 2.5 wt. % methyl acetate, was tested using this HI titration method. The HI concentrations varied from 50 wppm to 300 wppm. No portion of the light phase from the overhead light ends is recycled to the reactor. Without light phase recycle, the HI concentrations tend to be higher.

Example 1

Light Phase Recycle

A portion of light phase from the overhead light ends is recycled directly to the reactor to reduce the water content in the side stream. The side stream comprises about 1.5 wt. % water, about 3.6 wt. % methyl acetate, about 2.1 wt. % methyl iodide, with less than or equal to 25 wppm HI, and the balance comprising acetic acid, methyl acetate and methyl iodide. HI concentrations were too low to measure directly with titration. There are other cations present that makes directly measuring HI difficult. The measure of total inorganic iodide, i.e. total possible maximize HI, is done directly. These other inorganic iodides may include lithium iodide, as well as corrosion metal iodide.

What is claimed is:
1. A process for producing acetic acid comprising:
separating a reaction medium formed in a reactor in a flash vessel to form a liquid recycle and a vapor product stream, wherein the reaction medium comprises water in an amount from 0.1 to 4.1 wt. %;
distilling a portion of the vapor product stream in a first column to obtain a side stream, a low boiling overhead vapor stream comprising water in an amount of greater than or equal to 5 wt. %, and a residuum stream comprising acetic acid in an amount greater than or equal to 95 wt. % and water in an amount less than or equal to 5 wt. %;
condensing the low boiling overhead vapor stream and biphasically separating the condensed stream to form a heavy liquid phase and a light liquid phase;
maintaining a water concentration in the side stream from 1 to 3 wt. % and a hydrogen iodide concentration in the side stream of less than or equal to 50 wppm, based on the total weight of the side stream, by controlling a recycle rate of a portion of the light liquid phase to the reactor; and
distilling the side stream in a second column to obtain a purified acetic acid product.
2. The process of claim 1, wherein the reaction medium further comprises methyl acetate, a metal catalyst, an iodide salt and methyl iodide.
3. The process of claim 1, wherein the reaction medium comprises methyl acetate in an amount from 0.5 to 30 wt. %, a metal catalyst in an amount from 200 to 3000 wppm, iodide salt in an amount from 1 to 25 wt. %, and methyl iodide in an amount from 1 to 25 wt. %.
4. The process of claim 1, wherein a portion of the heavy liquid phase is treated to remove at least one permanganate reducing compound selected from the group consisting of acetaldehyde, acetone, methyl ethyl ketone, butylaldehyde, crotonaldehyde, 2-ethyl crotonaldehyde, 2-ethyl butyraldehyde, and the aldol condensation products thereof.
5. The process of claim 1, wherein the water concentration is maintained in the side stream from 1.1 to 2.5 wt. %.
6. The process of claim 1, wherein the hydrogen iodide concentration is maintained in the side stream from 0.1 to 50 wppm.
7. The process of claim 1, wherein the side stream further comprises one or more $C_1$-$C_{14}$ alkyl iodides in an concentration from 0.1 to 6 wt. % and the side stream further comprises methyl acetate in an concentration from 0.1 to 6 wt. %.
8. The process of claim 1, wherein the side stream comprises each of the one or more $C_1$-$C_{14}$ alkyl iodides and the methyl acetate in an amount within 0.9 wt. % of the water concentration in the side stream.
9. The process of claim 1, wherein the first column is operated with a reflux ratio from 0.05 to 0.4.
10. The process of claim 1, further comprising refluxing the heavy liquid phase, the light liquid phase, or a mixture thereof to the first column.
11. The process of claim 1, wherein the light liquid phase comprises water in an amount from 40 to 80 wt. %.
12. The process of claim 1, wherein the heavy liquid phase comprises water in an amount of less than or equal to 1 wt. %.
13. The process of claim 1, wherein the purified acetic acid product is withdrawn from the bottoms or near the bottoms of the second column.
14. The process of claim 1, wherein an aqueous overhead is withdrawn from the second column.
15. The process of claim 14, wherein the aqueous overhead comprises greater than or equal to 90% of the water in the side stream fed to the second column.
16. The process of claim 14, further comprising recycling the aqueous overhead, or a condensed portion thereof, to the reactor, wherein the recycle ratio of the mass flow of the light liquid phase recycled to the reactor to the mass flow of the aqueous overhead to the reactor is less than or equal to 2.
17. The process of claim 1, further comprising contacting the purified acetic acid product with a guard bed when total iodide concentration of the purified acetic acid product is less than or equal to 5 wppm.
18. The process of claim 1, wherein the recycle of light liquid phase is from 0 to 20%, of the total light phase condensed from the low boiling overhead vapor stream.
19. The process of claim 1, further comprising controlling an ethyl iodide concentration in the reaction medium at less than or equal to 750 wppm, and wherein the acetic acid product comprises less than 250 wppm propionic acid without directly removing propionic acid from the acetic acid product.

20. The process of claim 19, wherein ethyl iodide in the reaction medium and propionic acid in the acetic acid product are present in a weight ratio from 3:1 to 1:2.

21. The process of claim 19, wherein acetaldehyde and ethyl iodide are present in the reaction medium in a weight ratio from 2:1 to 20:1.

* * * * *